US009445876B2

(12) United States Patent
Ingmanson et al.

(10) Patent No.: US 9,445,876 B2
(45) Date of Patent: Sep. 20, 2016

(54) GLOVE WITH SENSORY ELEMENTS INCORPORATED THEREIN FOR CONTROLLING AT LEAST ONE SURGICAL INSTRUMENT

(71) Applicant: Covidien LP, Mansfield, MA (US)

(72) Inventors: Michael Ingmanson, Stratford, CT (US); John Ferraro, Stratford, CT (US)

(73) Assignee: Covidien LP, Mansfield, MA (US)

( * ) Notice: Subject to any disclaimer, the term of this patent is extended or adjusted under 35 U.S.C. 154(b) by 104 days.

(21) Appl. No.: 13/765,051

(22) Filed: Feb. 12, 2013

(65) Prior Publication Data

US 2013/0226168 A1    Aug. 29, 2013

Related U.S. Application Data

(60) Provisional application No. 61/603,395, filed on Feb. 27, 2012.

(51) Int. Cl.
*A61B 17/068* (2006.01)
*A61B 17/00* (2006.01)
*A61B 19/00* (2006.01)
*A61B 17/072* (2006.01)

(52) U.S. Cl.
CPC .............. *A61B 19/22* (2013.01); *A61B 17/068* (2013.01); *A61B 17/07207* (2013.01); *A61B 2017/00207* (2013.01)

(58) Field of Classification Search
CPC .......... A61B 19/22; A61B 2019/2273; A61B 2017/00017; A61B 2017/00207
USPC ................................ 606/34, 42; 600/15, 388
See application file for complete search history.

(56) References Cited

U.S. PATENT DOCUMENTS

| 3,845,771 | A | * | 11/1974 | Vise ................................ 606/49 |
| 4,414,537 | A | | 11/1983 | Grimes |
| 5,070,543 | A | * | 12/1991 | Beck .............................. 2/163 |
| 5,283,722 | A | * | 2/1994 | Koenen et al. .............. 362/570 |
| 5,350,391 | A | * | 9/1994 | Iacovelli ........ A61B 17/320016 606/167 |

(Continued)

FOREIGN PATENT DOCUMENTS

WO    WO 2005/092230 A2    10/2005

OTHER PUBLICATIONS

European Search Report dated Jun. 19, 2013 for European Patent Appln. No. EP 13 15 6670.

(Continued)

*Primary Examiner* — Christopher A Flory

(57) ABSTRACT

A surgical control system is provided including a glove having a plurality of sensory elements disposed therein, the plurality of sensory elements configured to provide sensory signals and at least one surgical instrument configured to be responsive to the sensory signals when the glove is within a functional range of the at least one surgical instrument. The plurality of sensory elements are magnetic elements or conductive elements. At least one surgical instrument includes a plurality of sensors positioned therein for sensing the magnetic elements or the conductive elements of the glove. Movement of the glove having the plurality of magnetic or conductive elements disposed therein, relative to the at least one surgical instrument, causes the plurality of sensors positioned within the at least one surgical instrument to activate at least one operation of the at least one surgical instrument.

16 Claims, 8 Drawing Sheets

(56) References Cited

U.S. PATENT DOCUMENTS

| | | | |
|---|---|---|---|
| 5,599,151 A * | 2/1997 | Daum | B25J 15/0009 294/111 |
| 5,715,539 A | 2/1998 | Benecki et al. | |
| 5,813,813 A * | 9/1998 | Daum | B25J 15/0009 294/111 |
| 5,986,643 A | 11/1999 | Harvill et al. | |
| 6,413,229 B1 | 7/2002 | Kramer et al. | |
| 6,443,968 B1 * | 9/2002 | Holthaus | A61B 17/320092 606/169 |
| 6,551,312 B2 * | 4/2003 | Zhang et al. | 606/41 |
| 6,569,163 B2 | 5/2003 | Hata et al. | |
| 6,924,787 B2 | 8/2005 | Kramer et al. | |
| 6,965,812 B2 | 11/2005 | Wang et al. | |
| 7,118,582 B1 | 10/2006 | Wang et al. | |
| 7,802,314 B2 | 9/2010 | Cohen | |
| 7,951,145 B2 | 5/2011 | Schneider | |
| 8,638,057 B2 * | 1/2014 | Goldberg et al. | 318/581 |
| 8,776,800 B2 * | 7/2014 | Skora | A61B 19/081 128/849 |
| 8,942,828 B1 * | 1/2015 | Schecter | A61N 1/05 607/116 |
| 9,023,071 B2 * | 5/2015 | Miller | A61B 17/320068 200/512 |
| 2002/0075232 A1 | 6/2002 | Daum et al. | |
| 2004/0046736 A1 | 3/2004 | Pryor et al. | |
| 2004/0097836 A1 | 5/2004 | Ombrellaro | |
| 2004/0230214 A1 | 11/2004 | Donofrio et al. | |
| 2004/0260281 A1 | 12/2004 | Baxter, III et al. | |
| 2005/0021050 A1 * | 1/2005 | Cooper | A61B 46/13 606/130 |
| 2006/0020167 A1 * | 1/2006 | Sitzmann | A61B 1/00039 600/173 |
| 2006/0087746 A1 | 4/2006 | Lipow | |
| 2006/0119578 A1 * | 6/2006 | Kesavadas | G06F 3/014 345/161 |
| 2008/0058836 A1 * | 3/2008 | Moll et al. | 606/130 |
| 2008/0140088 A1 * | 6/2008 | Orban, III | A61B 19/2203 606/130 |
| 2008/0167662 A1 | 7/2008 | Kurtz | |
| 2008/0215445 A1 * | 9/2008 | Horton et al. | 705/14 |
| 2008/0255505 A1 * | 10/2008 | Carlson et al. | 604/95.04 |
| 2009/0088774 A1 * | 4/2009 | Swarup et al. | 606/130 |
| 2009/0088775 A1 * | 4/2009 | Swarup et al. | 606/130 |
| 2009/0247993 A1 * | 10/2009 | Kirschenman et al. | 606/1 |
| 2009/0248038 A1 * | 10/2009 | Blumenkranz | B25J 13/085 606/130 |
| 2009/0282371 A1 | 11/2009 | Curl | |
| 2009/0326406 A1 * | 12/2009 | Tan et al. | 600/546 |
| 2010/0069940 A1 * | 3/2010 | Miller | A61B 17/320068 606/169 |
| 2010/0073150 A1 * | 3/2010 | Olson | A61B 19/2203 340/407.1 |
| 2010/0231509 A1 * | 9/2010 | Boillot et al. | 345/156 |
| 2011/0028860 A1 * | 2/2011 | Chenaux et al. | 600/554 |
| 2011/0066161 A1 * | 3/2011 | Cooper | A61B 46/13 606/130 |
| 2011/0118752 A1 | 5/2011 | Itkowitz et al. | |
| 2011/0118753 A1 * | 5/2011 | Itkowitz et al. | 606/130 |
| 2011/0144729 A1 * | 6/2011 | Weber | A61B 18/1402 607/99 |
| 2011/0148607 A1 * | 6/2011 | Zeleny | 340/407.1 |
| 2011/0152883 A1 * | 6/2011 | Reis | 606/130 |
| 2011/0242305 A1 * | 10/2011 | Peterson et al. | 348/77 |
| 2012/0038549 A1 * | 2/2012 | Mandella et al. | 345/156 |
| 2012/0071891 A1 * | 3/2012 | Itkowitz et al. | 606/130 |
| 2012/0071892 A1 * | 3/2012 | Itkowitz et al. | 606/130 |
| 2012/0123410 A1 * | 5/2012 | Craig | 606/41 |
| 2012/0179169 A1 * | 7/2012 | Swarup et al. | 606/130 |
| 2012/0188158 A1 * | 7/2012 | Tan et al. | 345/156 |
| 2012/0209293 A1 * | 8/2012 | Carlson et al. | 606/130 |
| 2012/0247489 A1 * | 10/2012 | Orban, III | A61B 19/2203 128/849 |
| 2012/0249310 A1 | 10/2012 | Hotaling | |
| 2012/0259239 A1 * | 10/2012 | Chenaux et al. | 600/554 |
| 2012/0265083 A1 * | 10/2012 | Schecter | 600/508 |
| 2012/0283745 A1 * | 11/2012 | Goldberg et al. | 606/130 |
| 2012/0323364 A1 * | 12/2012 | Birkenbach et al. | 700/257 |
| 2013/0006268 A1 * | 1/2013 | Swarup et al. | 606/130 |
| 2013/0046302 A1 * | 2/2013 | Schneider | A61B 19/04 606/42 |
| 2013/0172814 A1 * | 7/2013 | Olson et al. | 604/95.04 |
| 2013/0190741 A1 * | 7/2013 | Moll et al. | 606/13 |
| 2013/0321262 A1 * | 12/2013 | Schecter | 345/156 |
| 2013/0331650 A1 * | 12/2013 | Blumenkranz | A61B 19/2203 600/130 |
| 2014/0107627 A1 * | 4/2014 | Blumenkranz | A61B 90/10 606/1 |
| 2014/0121524 A1 * | 5/2014 | Chiang | A61B 8/0883 600/459 |
| 2014/0207010 A1 * | 7/2014 | Schecter | 600/508 |
| 2015/0157191 A1 * | 6/2015 | Phee | A61B 1/00133 600/106 |
| 2015/0157410 A1 * | 6/2015 | Kilroy | A61B 90/10 606/130 |
| 2015/0164598 A1 * | 6/2015 | Blumenkranz | A61B 19/2203 606/130 |
| 2015/0173731 A1 * | 6/2015 | Lohmeier | A61B 19/2203 606/1 |
| 2015/0173839 A1 * | 6/2015 | Lohmeier | A61B 19/2203 606/130 |
| 2015/0173840 A1 * | 6/2015 | Lohmeier | A61B 19/2203 606/130 |
| 2015/0173841 A1 * | 6/2015 | Orban | A61B 19/2203 606/130 |
| 2015/0250496 A1 * | 9/2015 | Kawaguchi | A61B 17/282 606/27 |
| 2016/0113731 A1 * | 4/2016 | Stokes | A61B 34/37 606/130 |

OTHER PUBLICATIONS

Chinese Office Action for CN 2013-10062493.7 dated Jan. 21, 2016.

* cited by examiner

GLOVE WITH SENSORY ELEMENTS INCORPORATED THEREIN FOR CONTROLLING AT LEAST ONE SURGICAL INSTRUMENT

CROSS REFERENCE TO RELATED APPLICATION

The present application claims the benefit of and priority to U.S. Provisional Application Ser. No. 61/603,395, filed on Feb. 27, 2012, the entire contents of which are incorporated herein by reference.

BACKGROUND

1. Technical Field

The present disclosure relates generally to the field of surgical instruments. In particular, the disclosure relates to one or more surgical instruments controlled by a magnetic glove worn by a user for manipulating the one or more surgical instruments.

2. Background of Related Art

Surgical instruments are commonly used in open and endoscopic surgical procedures to coagulate, cauterize and seal tissue. Such surgical instruments may typically include a pair of jaws that may be controlled by a surgeon to grasp targeted tissue, such as, e.g., a blood vessel. The jaws may be approximated to apply a mechanical clamping force to the tissue, and may be associated with at least one electrode surface to permit the delivery of electrosurgical energy to tissue. The combination of the mechanical clamping force and the electrosurgical energy has been demonstrated to join adjacent layers of tissue captured between the jaws.

Presently, many electrosurgical instruments are costly to manufacturers, hospitals, and patients, due to the number of parts present in these instruments. Such electrosurgical instruments have become more and more complex by including a plurality of different functions actuated by a plurality of different switches and/or buttons placed throughout the exterior surface of the instrument. The plethora of switches and/or buttons may detract the surgeon's attention from the surgery. Thus, a need has arisen for electrosurgical instruments that are cost effective, yet give surgeons the control and range of motion necessary to successfully perform a wide variety of medical procedures without causing unnecessary distractions during the surgical procedures.

SUMMARY

Accordingly, a surgical control system is provided. The surgical control system includes a glove including a plurality of sensory elements disposed therein, the plurality of sensory elements configured to provide sensory signals and at least one surgical instrument configured to be responsive to the sensory signals when the glove is within a functional range of the at least one surgical instrument.

In one exemplary embodiment, the plurality of sensory elements are placed on a finger region of the glove. In an alternate exemplary embodiment, the plurality of sensory elements are placed on a palm region of the glove. The plurality of sensory elements placed on the palm region of the glove may be adapted to be power indicators.

In yet another exemplary embodiment, the plurality of sensory elements are conductive elements. The at least one surgical instrument includes a plurality of conductive sensors positioned therein for sensing the conductive elements of the glove. In an alternate exemplary embodiment, the plurality of sensory elements are magnetic elements. The at least one surgical instrument includes a plurality of magnetic sensors positioned therein for sensing the magnetic elements of the glove.

Movement of the glove having the plurality of magnetic elements disposed therein, relative to the at least one surgical instrument, causes the plurality of magnetic sensors positioned within the at least one surgical instrument to activate at least one operation of the at least one surgical instrument. Stated otherwise, the glove slidably maneuvers over one or more surfaces of the at least one surgical instrument to trigger one or more functions of the at least one surgical instrument.

Additionally, an exterior surface of the at least one surgical instrument is devoid of any switches and buttons or has a reduced number of switches or buttons due to signal control by the glove. Moreover, an exterior surface of the at least one surgical instrument may include a plurality of textured control surfaces indicating control boundaries, wherein the surgical instrument includes a plurality of sensors disposed throughout, and wherein the plurality of sensors receive sensory signals from the plurality of sensory elements of the glove.

In another exemplary embodiment a method of controlling at least one surgical instrument is presented. The method includes the steps of providing sensory signals via a plurality of sensory elements disposed within a glove; placing the glove within a functional region of the at least one surgical instrument, wherein the at least one surgical instrument includes a plurality of sensors; triggering the plurality of sensors via the plurality of sensory elements; and activating at least one operation of the at least one surgical instrument in response to the sensory signals received by the plurality of sensors.

Accordingly, a surgical control system is provided. The surgical control system includes a wearable article including a plurality of sensory elements incorporated thereon and at least one medical device having a plurality of sensors placed therein, wherein the at least one medical device is devoid of or has a reduced number of exterior switches and buttons, and wherein the at least one medical device is configured to allow wireless communication between the plurality of sensory elements and the plurality of sensors for triggering one or more functions of the at least one medical device.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figures 1A, 1B:
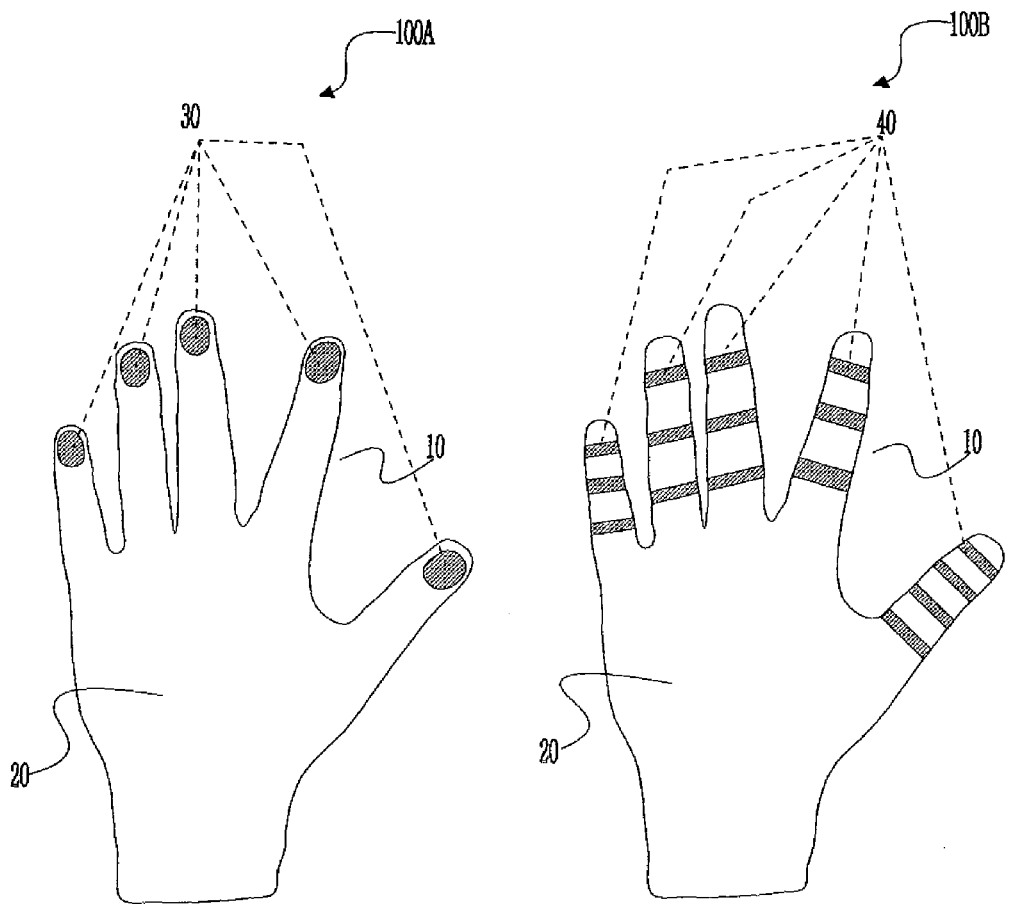
FIG. 1A illustrates a glove for controlling a surgical instrument, the glove including a plurality of sensory elements at the fingertip portion of the glove, in accordance with the present disclosure.
FIG. 1B illustrates a glove for controlling a surgical instrument, the glove including a plurality of sensory elements configured to be in a ring configuration disposed across a length of the finger portion of the glove, in accordance with an embodiment of the present disclosure.

Particular embodiments of the present disclosure are described hereinbelow with reference to the accompanying drawings. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Embodiments of the presently disclosed apparatus will now be described in detail with reference to the drawings, in which like reference numerals designate identical or corresponding elements in each of the several views. As used herein, the term "distal" refers to that portion of the tool, or component thereof which is further from the user while the term "proximal" refers to that portion of the tool or component thereof which is closer to the user.

As it is used in this description, "finger" generally refers to the terminating members of the hand including the thumb. In general, the term "finger" is interchangeable, in this disclosure, with the terms "surgeon's finger" and "user's finger."

Referring to FIG. 1A, a glove 100A for controlling a surgical instrument is presented, glove 100A including a plurality of sensory elements 30 at the fingertip portion of glove 100A, in accordance with the present disclosure.

In particular, glove 100A includes a plurality of finger regions 10 and a palm region 20. Each finger region 10 includes sensory elements 30, wherein a sensory element 30 is positioned on the tip of each finger region 10.

Referring to FIG. 1B, a glove 100B for controlling a surgical instrument is presented, glove 100B including a plurality of sensory elements 40, configured to be in a ring configuration, disposed across the length of the finger portion of glove 100B, in accordance with the present disclosure.

In particular, glove 100B includes a plurality of finger regions 10 and a palm region 20. Each finger region 10 includes a plurality of sensory elements 40, wherein a plurality of sensory elements 40 are positioned or placed or disposed across the length of each finger region 10. In accordance with the present disclosure, it is contemplated that sensory elements 40 extend at least partially across finger regions 10.

Figure 1C:
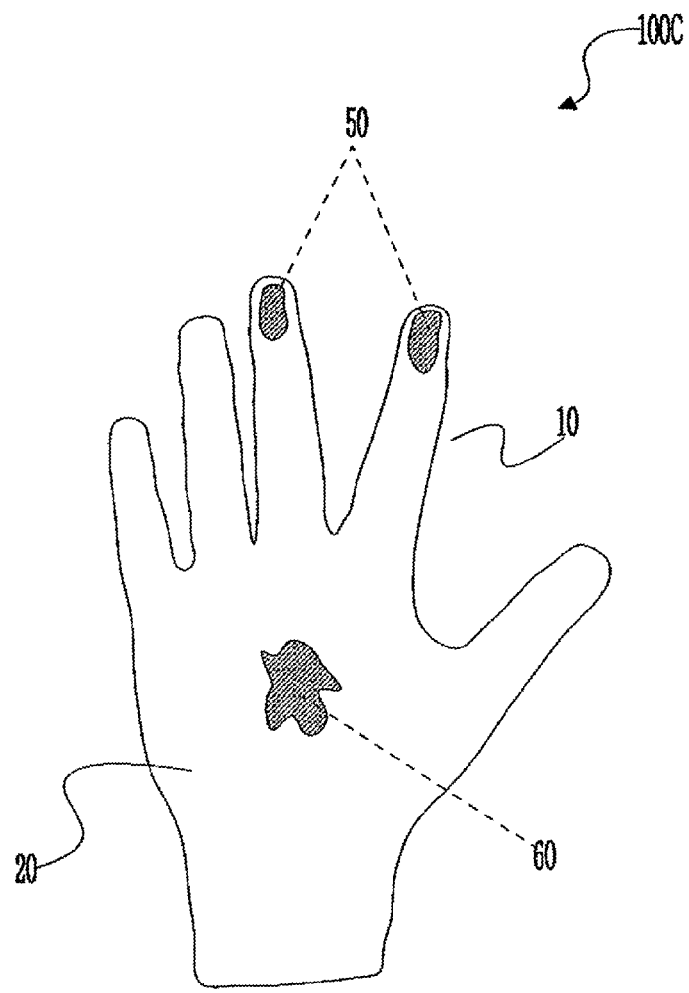
FIG. 1C illustrates a glove for controlling a surgical instrument, the glove including sensory elements positioned on two fingertip portions of the glove and a palm region of the glove, in accordance with a further embodiment of the present disclosure.

Referring to FIG. 1C, a glove 100C for controlling a surgical instrument is presented, glove 100C including sensory elements 50 positioned on two fingertip portions of glove 100C and a sensory element 60 positioned at a palm region 20 of glove 100C, in accordance with the present disclosure.

In particular, glove 100C includes a plurality of finger regions 10 and a palm region 20, wherein less than all finger regions 10 include a respective sensory element 50, wherein sensory elements 50 are positioned on two finger tips of finger region 10. For example, sensory elements 50 may be positioned on the finger tips of the middle finger and the index finger. Additionally, sensory element 60 may be placed in palm region 20.

Figures 2A, 2B:
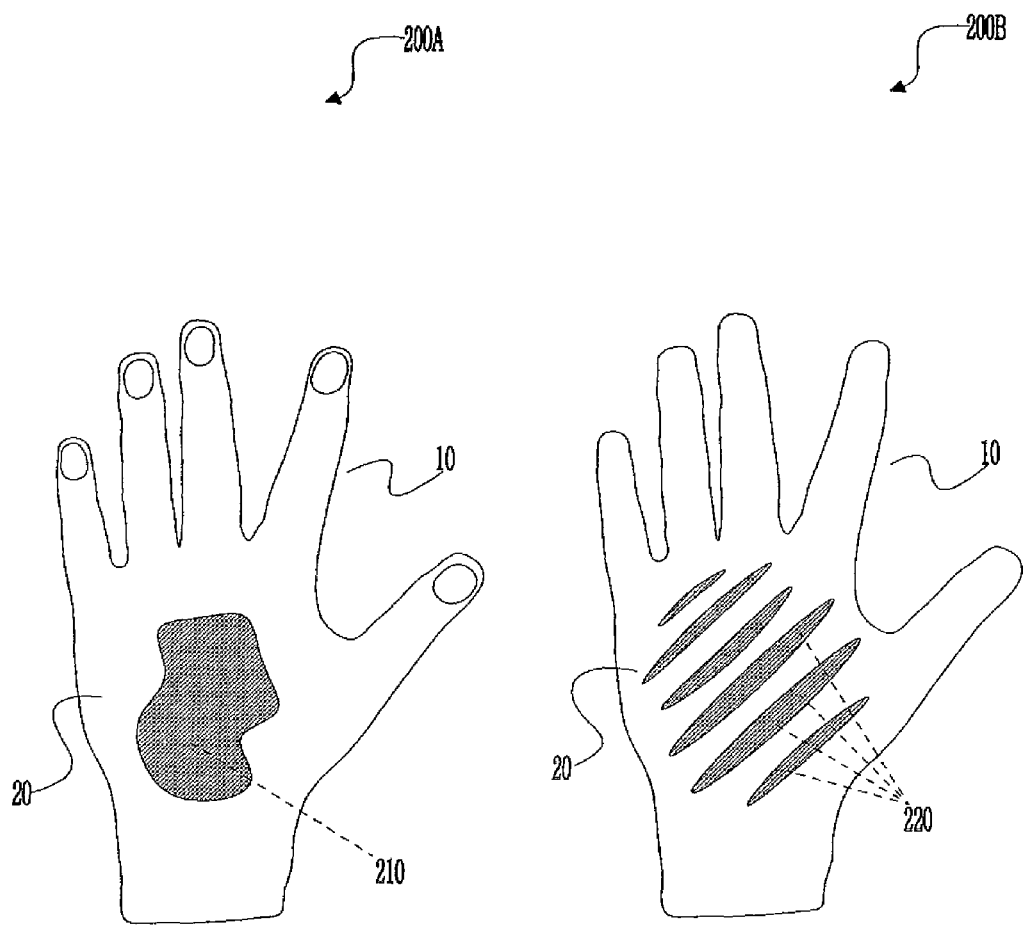
FIG. 2A illustrates a glove for controlling a surgical instrument, the glove including a single sensory element at the palm region of the glove, in accordance with yet another embodiment of the present disclosure.
FIG. 2B illustrates a glove for controlling a surgical instrument, the glove including a plurality of sensory elements at the palm region of the glove configured to be in a strip configuration, in accordance with still another embodiment of the present disclosure.

Referring to FIG. 2A, a glove 200A for controlling a surgical instrument is presented, glove 200A including a single sensory element 210 at palm region 20 of glove 200A.

In particular, glove 200A includes a plurality of finger regions 10 and a palm region 20, wherein in the present embodiment, finger region 10 includes no sensory elements. As seen in FIG. 2A, a single sensory element 210 is positioned in palm region 20, wherein sensory element 210 may be adapted to be a power indicator or one or more power indicators.

Referring to FIG. 2B, a glove 200B for controlling a surgical instrument is presented, glove 200B including a plurality of sensory elements 220 at palm region 20 of glove 200B, with the plurality of sensory elements 220 being configured to be in a strip configuration, in accordance with the present disclosure.

In particular, glove 200B includes a plurality of finger regions 10 and a palm region 20. According to the present embodiment, finger region 10 of glove 200B includes no sensory elements. Also, as seen in FIG. 2B, a plurality of sensory elements 220 positioned in palm region 20, may be substantially equally spaced apart from one another, may have different lengths, and may be oriented in a diagonal orientation.

Therefore, as illustrated in FIGS. 1A-2B, a plurality of sensory elements 30, 40, 50, 60, 210, 220 may be positioned in various regions of gloves 100A, 100B, 100C, 200A, 200B as contemplated by one skilled in the art. The plurality of sensory elements 30, 40, 50, 60, 210, 220 may be embedded, incorporated, positioned, placed or disposed on or within one or more portions or segments of gloves 100A, 100B, 100C, 200A, 200B. Thus, the plurality of sensory elements 30, 40, 50, 60, 210, 220 may be placed on inner or outer portions of gloves 100A, 100B, 100C, 200A, 200B described herein. The plurality of sensory elements 30, 40, 50, 60, 210, 220 may be constructed to be any shape or size, as contemplated by one skilled in the art.

The construction of gloves 100A, 100B, 100C, 200A, 200B described with reference to FIGS. 1A-2B may include any suitable material such as, without limitation, a non-woven material, a woven material or fabric, a film, or a laminate or other combination of these materials. For example, the material may be formed of natural latex, synthetic latex, or a dissolved elastomeric polymer, such as a natural rubber, a nitrile rubber, a polyurethane, a homopolymer of a conjugated diene, a copolymer of a least two conjugated dienes, a copolymer of at least one conjugated diene and at least one vinyl monomer, or any other suitable combinations thereof. If the material is a non-woven material, the non-woven material may suitably include a fibrous non-woven web, which, as used herein, refers to a structure of individual fibers or filaments randomly arranged in a mat-like fashion that may but need not necessarily include a binder material to facilitate binding together of the fibers. The fibrous non-woven substrate may be formed from a single web layer or multiple web layers.

Moreover, where the material includes multiple layers, the layers are generally positioned in a juxtaposed or surface-to-surface relationship and all or a portion of the layers may be bound to adjacent layers. The multi-layers may be of the same material or of different materials. For example, the material of the gloves may include a non-woven web that is laminated or otherwise secured to a film, a woven material or a different non-woven web, without departing from the scope of the present disclosure.

The surgical gloves described herein may be configured to be fit onto a human hand. The surgical gloves may be configured to fit onto a right hand or a left hand. The surgical gloves may be formed from any appropriate flexible material, such as, but not limited to, latex and non-latex materials, as described above. The surgical gloves may be disposable or reusable. The surgical gloves may also include antibacterial agents, such as a coating or other appropriate applications. The gloves may be able to be sterilized with conventional techniques.

Figure 3A:
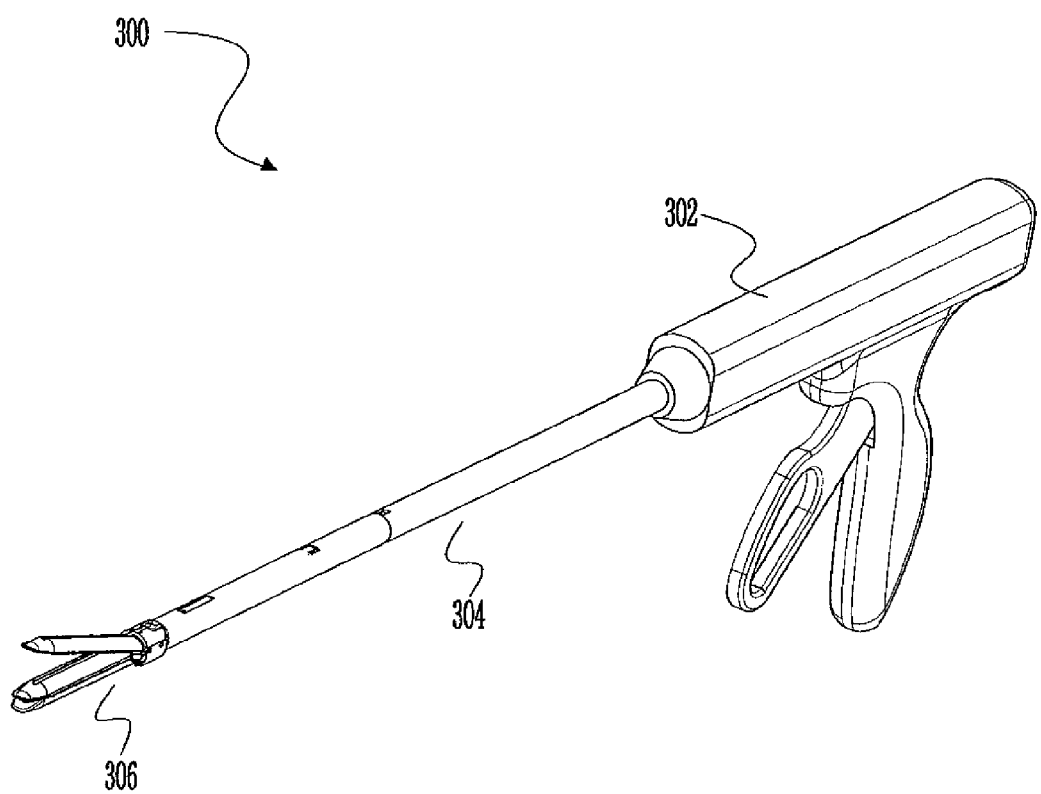
FIG. 3A illustrates a surgical instrument including a jaw member disposed at a distal end thereof, the surgical instrument devoid of any buttons and/or switches on its exterior surface, in accordance with another embodiment of the present disclosure.

Referring to FIG. 3A, a surgical instrument 300 including a jaw member disposed at a distal end thereof is presented, the surgical instrument 300 devoid of any buttons and/or switches, in accordance with the present disclosure.

Surgical instrument 300 includes handle portion 302, a shaft portion 304 connected to and extending from handle portion 320, and an end effector 306 extending from and connected to shaft portion 304. In this exemplary embodiment, end effector 306 is a jaw mechanism. However, one skilled in the art may contemplate using a plurality of other well known end effectors. For example, some surgical instruments may be provided with a pair of jaws on the distal end to grasp or cut various tissues. Operation of the handle assembly opens and closes the jaws by transmitting a force from a trigger mechanism associated with the handle assembly to the jaws and thus to the tissue. Other types of surgical instruments may be provided including instruments having fastener applying end effectors, which are configured to apply staples, clips, or other fasteners to tissue, and instruments that apply electrosurgical energy to seal and/or fuse tissue.

A seen in FIG. 3A, surgical instrument 300 does not include any buttons and/or switches on its exterior surface. In other words, the exterior surface of surgical instrument 300 is devoid of any mechanical input mechanisms. However, the exterior surface of the surgical instrument may include a plurality of textured control surfaces indicating control boundaries (see FIGS. 4A, 4B).

Figure 3B:
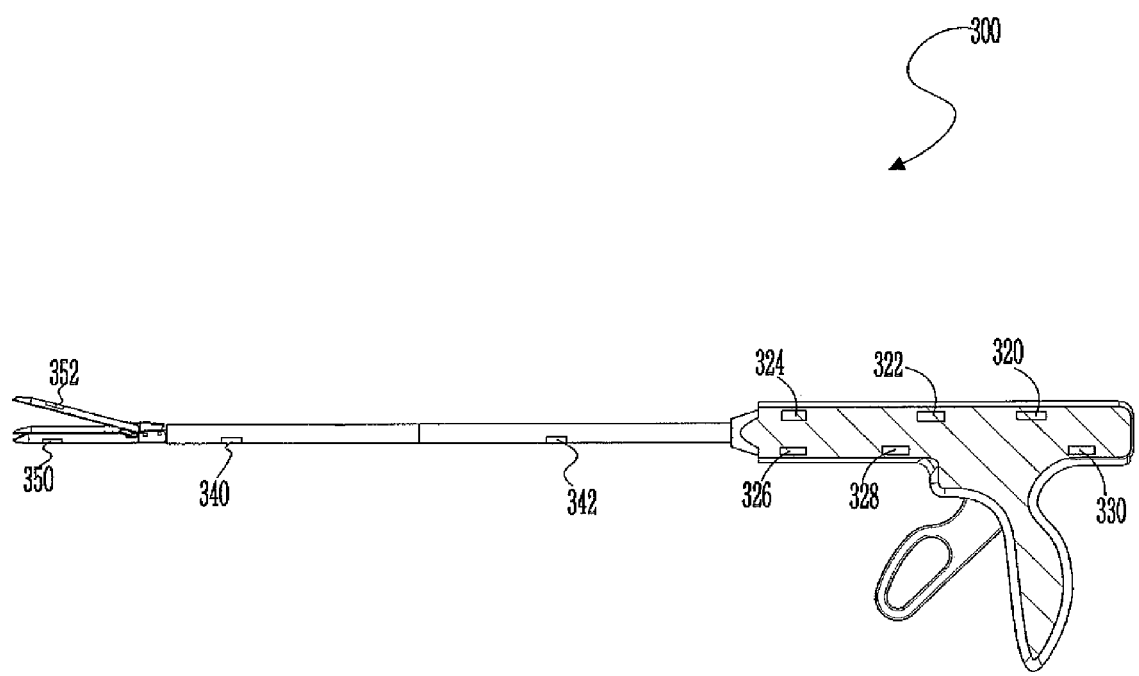
FIG. 3B illustrates a cross-sectional view of the surgical instrument of FIG. 3A, where a plurality of sensors are positioned within the surgical instrument to interact with one or more sensory elements of the gloves shown in FIGS. 1A-2B, in accordance with an embodiment of the present disclosure.

Referring to FIG. 3B, a cross-sectional view of the surgical instrument 300 of FIG. 3A is presented, where a plurality of sensors are positioned within the surgical instrument 300 to interact with one or more gloves shown in FIGS. 1A-2B, in accordance with the present disclosure.

A seen in FIG. 3B, there is depicted a plurality of sensors positioned within the interior portions of surgical instrument 300 of FIG. 3A. For example, handle portion 302 may include one or more sensors 320, 322, 324, 326, 328, 330 positioned across the length thereof and/or at various discrete locations around handle portion 302. Shaft portion 304 may include one or more sensors 340, 342, whereas end effector 306 may include one or more sensors 350, 352 (e.g., at least one on the first jaw member and one on the second jaw member). One skilled in the art may contemplate incorporating a plurality of different sensors throughout the length and width of the interior portions of surgical instrument 300.

In one exemplary embodiment, the gloves may be worn by a surgeon for performing electrosurgery on a patient. The plurality of sensory elements of the gloves are configured to generate sensory signals when brought into proximity of or moved relative to the sensors of surgical instrument 300. In accordance with the present disclosure, the plurality of sensory elements may be magnetic elements or the like. In particular, in an embodiment, it is contemplated that the plurality of sensory elements are conductive elements.

The plurality of sensory elements may be magnetic sensors. The plurality of sensory elements may be Hall Effect sensors. A Hall Effect sensor is a transducer that varies its output in response to changes in magnetic field. The plurality of sensory elements may be able to detect changes in the proximity of the gloves to surgical instrument 300.

The sensory signals generated are configured to communicate with a plurality of sensors, such as Hall Effect sensors described above, positioned within the surgical instrument used by the surgeon (see FIGS. 3A, 3B). The sensory signals may be wirelessly transmitted between the gloves and the surgical instrument in order to control one or more operations of the surgical instrument through motion or gesture control mechanisms, as described in detail further below.

For instance, several communicating/signaling methods for activating operations of the wireless electrosurgical instrument may be available. The communicating/signaling method of the present disclosure may be selected from a group consisting of at least (a) infrared transmission, (b) short range radio frequency signaling, and (c) a monopolar end effector using capacitive coupling of signals. Other communication/signal transmission methods, such as ultrasound, light, laser, or the like are also applicable in the present disclosure. One skilled in the art may contemplate using any type of wireless communication technologies to allow for bilateral communication between at least one glove and at least one surgical instrument.

Concerning infrared transmission, infrared transmission techniques may use infrared Light Emitting Diodes (LEDs) to transmit light pulses to perform the signaling and communication. Different signals for cutting, coagulating, inactive, or other functions may be made available by varying the flashing frequency or other timing characteristics.

Concerning short range communications, this communication may be performed at very short range from one or several LEDs, possibly being arranged to form an optimized spreading of the light power, aimed at a receiver on the surgeon's glove.

Concerning capacitive coupling, another alternative is the one which integrates the signal and power delivery into the same conductor. This eliminates the requirement of a second set of wires on the user and the inconvenience of positioning them and maintaining appropriate orientations. The transmitter in the wireless instrument in the user's hands and the receiver in the glove are connected directly through a single conductor. The transmitter may include circuitry to create voltage pulses of different time lengths depending on which task, for example, cut or coagulate, that the user wishes to perform.

Therefore, the plurality of sensors shown in FIG. 3B are configured to be responsive to sensory signals generated by the sensory elements disposed within the gloves (see FIGS. 1A-2B), when gloves 100A, 100B, 100C, 200A, 200B are within a functional range of surgical instrument 300. Movement of gloves 100A, 100B, 100C, 200A, 200B having a plurality of sensory elements 30, 40, 50, 60, 210, 220 disposed therein causes the plurality of sensors 320, 322, 324, 326, 328, 330, 340, 342, 350, 352 positioned within surgical instrument 300 to activate at least one operation of surgical instrument 300. Stated otherwise, gloves 100A, 100B, 100C, 200A, 200B slidably maneuver over one or more surfaces of surgical instrument 300 to trigger one or more functions of surgical instrument 300. Thus, if magnetic sensors are located within surgical instrument 300, the magnetic sensors sense when a specific magnetic field is present (i.e., induced by proximity of magnetically embedded sensing elements in one of the gloves described herein). The sensing of this field triggers surgical instrument 300 to perform or enable or execute one or more operations or functions.

Figure 4A:
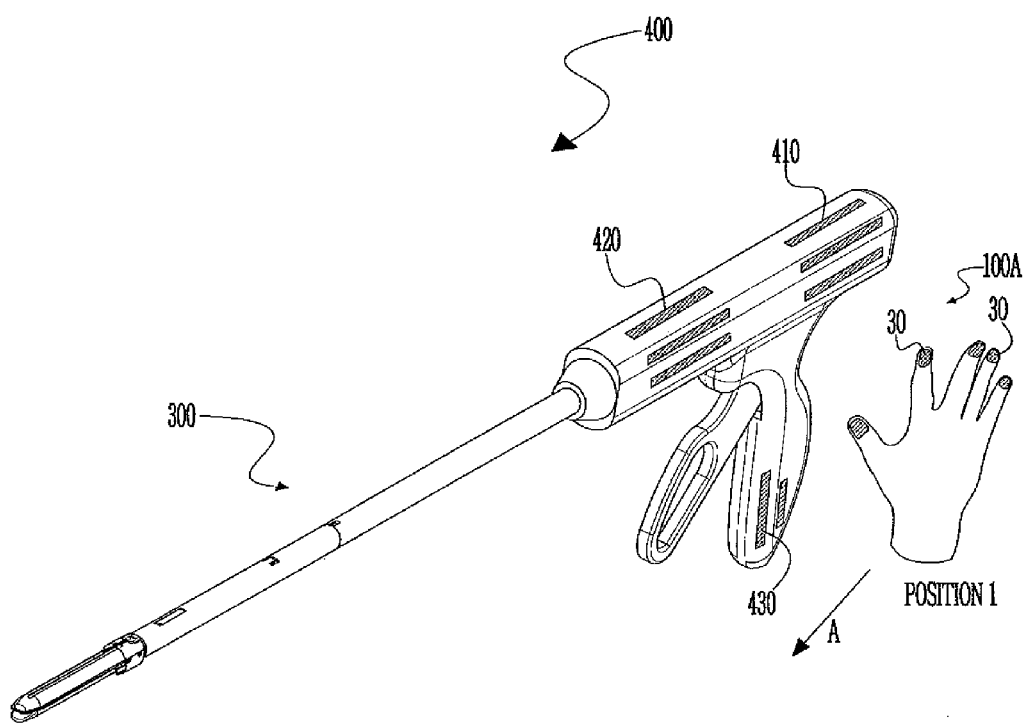
FIG. 4A illustrates the glove shown in FIG. 1A in a first position with respect to the surgical instrument, where the glove has not activated a sensor located within the surgical instrument, in accordance with an embodiment of the present disclosure.
Figure 4B:
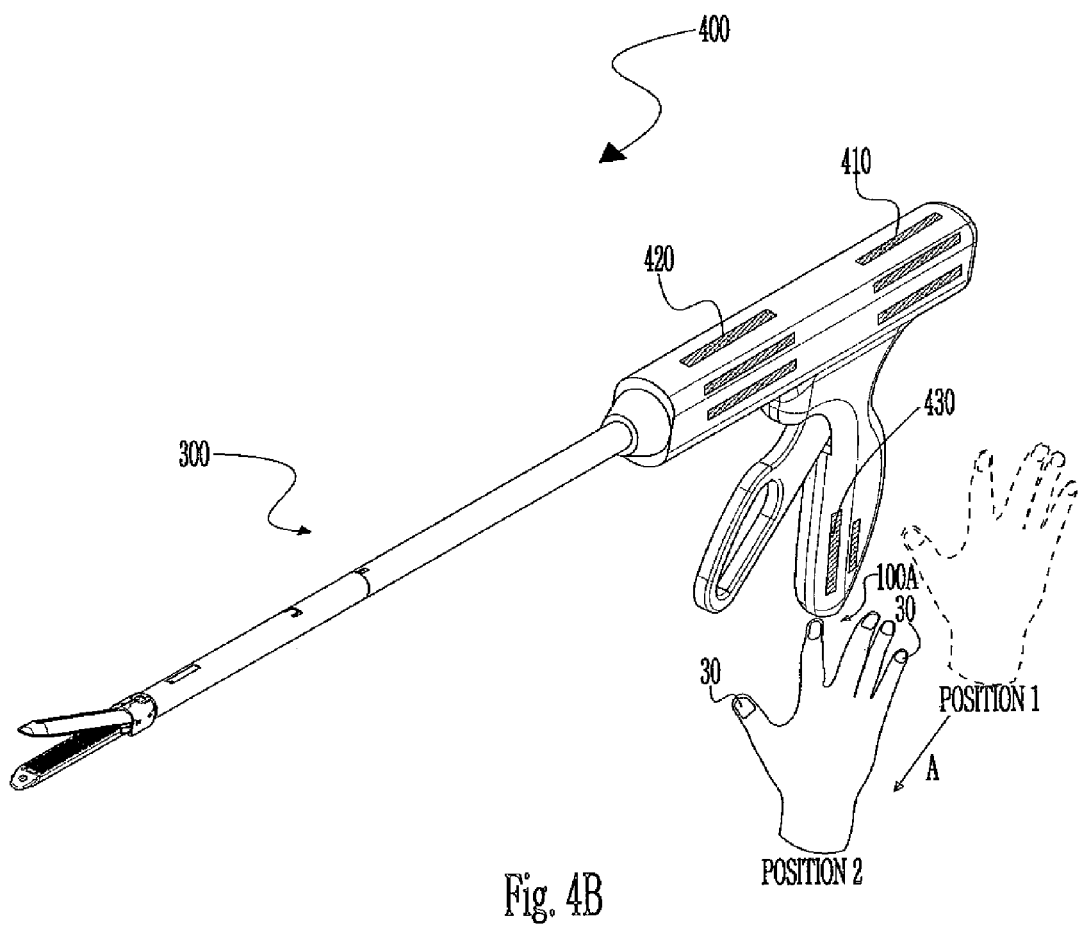
FIG. 4B illustrates the glove of FIG. 4A in a second position with respect to the surgical instrument, where the glove approaches the surgical instrument to actuate sensors embedded within the surgical instrument to interact with the sensors to activate at least one operation of the surgical instrument, in accordance with an embodiment of the present disclosure.

Referring to FIGS. 4A and 4B, glove 100A shown in FIG. 1A, is presented advancing from a first position to a second position with respect to surgical instrument 300 in order to activate at least one operation of surgical instrument 300, in accordance with the present disclosure.

In surgical control system 400, surgical instrument 300 includes a plurality of first textured control surfaces 410, a plurality of second textured control surfaces 420, and a plurality of third textured control surfaces 430 positioned on the handle portion of surgical instrument 300. Of course, one skilled in the art may contemplate a different number of textured surfaces spanning the length or width of the surgical instrument. Textured control surfaces 410, 420, 430 indicate regions under which sensors, as described above, have been placed. For example, such intended control areas may be manufactured with a polished finish, whereas non-control areas or surfaces may be manufactured with a rough finish.

Textured control surfaces 410, 420, 430 may be used to communicate intended control boundaries and hand positioning in a tactile manner. This would allow for surgical instrument operation that does not require direct observation of the control surface by the surgeon.

Thus, through the use of the gloves (see FIGS. 1A-2B) and the associated control surfaces (see FIGS. 4A-4C) and the underlying sensors (see FIG. 3B) of surgical instrument 300, the user is able to control and/or manipulate operations and/or functions of the surgical instrument 300. For example, a user may move his finger, or his entire hand from a first position to a second position, as indicated by arrow "A," or may tap his fingers against discreet areas of surgical instrument 400, in order to activate any of the sensors associated with the third textured control surface 430. Of course, it is contemplated that a plurality of surgical instruments may be simultaneously or contemporaneously controlled in a similar manner.

Optionally, these textured surfaces may include a plurality of different geometric features or patterns, which aid the surgeon in positioning his/her fingers on the surgical instrument. The geometric features may be any size contemplated by one skilled in the art.

In one aspect of the present disclosure, hand tracking of at least a part of the hand of the surgeon is used by a hand tracking controller (not shown) disposed within the surgical instrument to determine whether a hand gesture pose is made by the surgeon, or a combination of a hand gesture pose, and a hand gesture trajectory is made by the surgeon. Each hand gesture pose and each hand gesture trajectory combined with a hand gesture pose may be mapped to a different system command. The system commands control, for example, system mode changes and control other aspects of the minimally invasive surgical system. As used herein, a hand gesture, or gesture, includes, and is not limited to, a hand gesture pose, a hand gesture trajectory, and a combination of a hand gesture pose and a hand gesture trajectory.

In another aspect of the present disclosure, hand tracking sensors embedded within the surgical instrument (see FIG. 3B) may determine the position and/or orientation of the surgeon's hand. If the difference in the two positions is within a predetermined distance, e.g., less than a threshold separation, activation of at least one operation/function is permitted. Otherwise activation of any functions/operations is inhibited. Thus, distance may be used as a measure of presence of the surgeon's hand with respect to the surgical instrument. The distance may be a predetermined distance (preset during manufacturing of the instrument) or may be set by the surgeon, after manufacturing of the instrument.

As a result, the plurality of sensors within surgical instrument 300 track the location of a human hand wearing a glove (see FIGS. 1A-2B) incorporating a plurality of sensory elements 30, 40, 50, 60, 210, 220. Operations of surgical instrument 300 are controlled by sensory elements 30, 40, 50, 60, 210, 220 of gloves 100A, 100B, 100C, 200A, 200B and/or by motion of gloves 100A, 100B, 100C, 200A, 200B with respect to surgical instrument 300. Sensors 30, 40, 50, 60, 210, 220 in surgical instrument 300 may capture, x, y, z, yaw, pitch, roll position, and orientation information of gloves 100A, 100B, 100C, 200A, 200B. Thus, the term "location" may include both a position and orientation of gloves 100A, 100B, 100C, 200A, 200B relative to surgical instrument 300.

As one example of gesture-based control, a gesture-based control apparatus, e.g., a camera or imaging device (not shown), may be adapted to detect and "read" or recognize a clinician's or surgeon's specific hand-movements, and/or finger-pointing and/or gesturing to control which operations of the surgical instrument to activate. As another example, a clinician or system operator may wear one or a pair of gloves, which have a specific pattern, material, a light-emitting device, or a design embossed, printed, disposed on, or dyed into the glove. An imaging system and/or sensors embedded within the surgical instruments may detect the specific pattern, light-emitting device or design and execute commands representative of gestures received from the glove.

The ability to generate system commands using hand gestures (e.g., hand gesture poses or trajectories, as described above), in place of manipulating switches, buttons, foot pedals, etc. provides greater ease of use of the surgical instrument for the surgeon. When a surgeon is standing, the use of hand gesture poses and hand gesture trajectories to control the surgical instrument makes it is less necessary for the surgeon to take the surgeon's eyes off the patient and/or viewing screen and to search for a foot petal or a switch or a button when the surgeon wants to activate one or more functions/operations of the surgical instrument/ medical device. The particular set of hand gesture poses and hand gesture trajectories used to control the minimally invasive surgical system are not critical so long as each hand gesture pose and each hand gesture trajectory is unambiguous. Specifically, one hand gesture pose should not be able to be interpreted by the hand tracking controller as one or more other hand gesture poses in the set of poses, and one hand gesture trajectory should not be interpreted as more than one hand gesture trajectory in the set of trajectories.

Figure 4C:
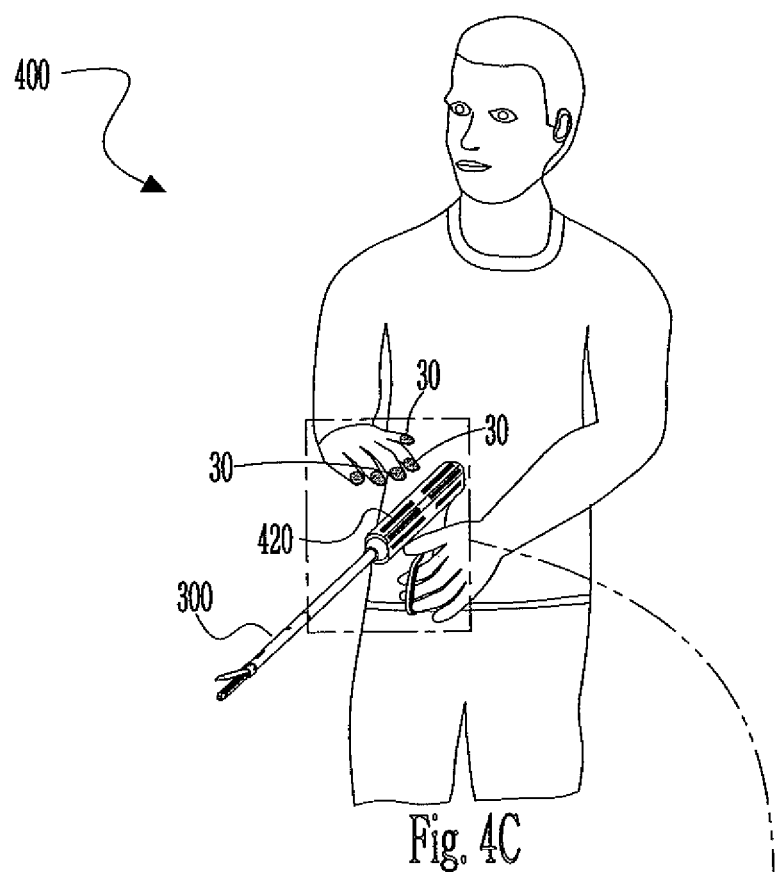
FIGS. 4C and 4D illustrate the glove of FIG. 4A sliding along a textured surface of the surgical instrument in order to vary an operation that is being performed, where at least one textured surface includes a plurality of bars which indicate a usage level of a variable activated, in accordance with an embodiment of the present disclosure.
Figure 4D:
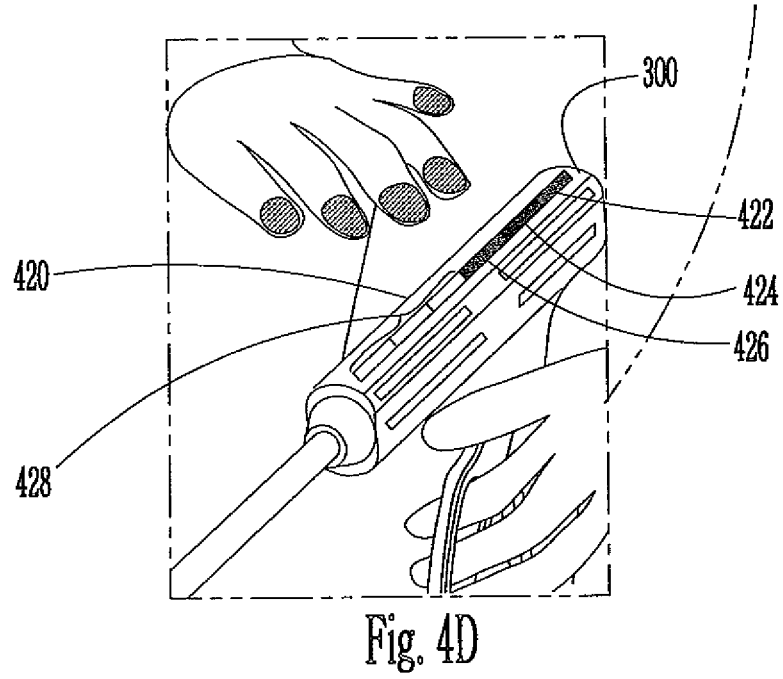

Referring to FIGS. 4C and 4D, a glove is presented sliding along a textured surface 420 of the surgical instrument 300 in order to vary an operation that is being performed, where at least one textured surface 420 includes a plurality of bars 422, 424, 426, 428 which indicate a usage level of a variable activated, in accordance with the present disclosure.

In FIG. 4C, the user is wearing one of the gloves described above (see FIGS. 1A-2B) that has sensory elements 30, 40, 50, 60, 210, 220. As the clinician or surgeon moves his hand wearing the glove along textured control surface 420, he has the capability to control a usage level or intensity level of an operative parameter. For example, textured control surface 420 may pertain to clamping pressure. The user may slide his finger over three bars 422, 424, 426 to set the pressure applied to tissue clamped by end effector 306 (see FIG. 3A). Bars 428 have not been activated. As such, in the instant case, the user may apply average pressure to clamp the tissue. Additionally, as another example, textured surface 420 may pertain to illumination strength. The user may slide his finger over three bars 422, 424, 426 to set the illumination intensity of a camera positioned at end effector 306 (see FIG. 3A). Of course, one skilled in the art may contemplate manipulating and/or controlling and/or adjusting a plurality of different variables and/or parameters represented by one or more textured control surfaces positioned across the length of surgical instrument 300 (see FIG. 3A).

In summary, the surgical control systems of the present disclosure may include a wearable article or garment (e.g., a glove) including a plurality of sensory elements incorporated thereon and at least one medical device (i) having a plurality of sensors placed therein, (ii) devoid of any exterior switches and buttons, and (iii) configured to allow wireless communication between the plurality of sensory elements and the plurality of sensors for triggering one or more functions and/or operations of the at least one medical device.

The advantages of the present disclosure may include, but are not limited to, improving the ability to manufacture and design "clam-shell" surgical instruments. By design, the surgical instrument of the present disclosure may be constructed with a smooth outer surface without the need to incorporate exterior switches and/or buttons onto the surgical instrument. Moreover, sterilization and cleaning procedures may be streamlined by reducing the need to sterilize or clean buttons, switches (or surgical instrument protrusions, recesses) and of smaller areas/surfaces therebetween.

Additionally, because of the non-fixed nature of the surgeon's hand, increased input control may be achieved. With the magnetic control glove, the user may readily input varying levels of intended output to the surgical instrument. For example, a finger could be slid up and down a series of sensors embedded within the surgical instrument (and not visible to the surgeon). This sensor setup would dynamically increase or decrease the speed at which the surgical instrument performs one or more operations/functions. The same control mechanism would also control the position of an end effector, moving it forward or backwards proportionally to the surgeon's finger position over the textured control surfaces. Moreover, with the elimination of buttons and/or switches from the exterior surface of the surgical instrument, the surgical instrument would reduce the likelihood for glove cutting/tearing on sharp edges. This would result in a safer surgical instrument for both the surgeons, as well as the patients.

The gloves described herein may also be provided with one or more additives or coatings that provide a benefit to the skin of a wearer. For instance, the additive or coating may comprise an anti-microbial agent, a bacteriostatic agent, a liquid absorption agent, a medicament, a therapeutic agent, mixtures thereof and the like. Examples of other therapeutic agents include various cosmetic agents, bath oils, hand lotions, aloe vera, and the like.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure. As well, one skilled in the art will appreciate further features and advantages of the present disclosure based on the above-described embodiments. Accordingly, the present disclosure is not to be limited by what has been particularly shown and described, except as indicated by the appended claims.

The invention claimed is:

1. A surgical control system, comprising:
a glove including a plurality of sensory elements disposed therein, the plurality of sensory elements configured to transmit signals; and
at least one handheld surgical instrument having an end effector and configured to receive the signals transmitted from the plurality of sensory elements of the glove such that the end effector is controlled directly from motions of the glove as the glove moves directly over one or more surfaces of the at least one handheld surgical instrument.

2. The control system according to claim 1, wherein the plurality of sensory elements are placed on a finger region of the glove.

3. The control system according to claim 2, wherein the plurality of sensory elements are placed in a ring configuration.

4. The control system according to claim 1, wherein the plurality of sensory elements are placed on a palm region of the glove.

5. The control system according to claim 1, wherein the signals transmitted by the plurality of sensory elements are electromagnetic signals.

6. The control system according to claim 1, wherein the plurality of sensory elements are conductive elements.

7. The control system according to claim 6, wherein the at least one surgical instrument includes a plurality of conductive sensors positioned therein for sensing the conductive elements of the glove.

8. The control system according to claim 1, wherein the plurality of sensory elements are magnetic elements.

9. The control system according to claim 8, wherein the at least one surgical instrument includes a plurality of magnetic sensors positioned therein for sensing the magnetic elements of the glove.

10. The control system according to claim 1, wherein an exterior surface of the at least one surgical instrument is devoid of any switches and buttons.

11. The control system according to claim 1, wherein an exterior surface of the at least one surgical instrument includes a plurality of textured control surfaces indicating control boundaries, wherein the at least one surgical instrument includes a plurality of sensors disposed throughout.

12. A method of controlling at least one handheld surgical instrument having an end effector, the method comprising:
providing sensory signals via a plurality of sensory elements disposed within a glove;
placing the glove within a functional region of the at least one handheld surgical instrument, wherein the at least one handheld surgical instrument includes a plurality of sensors positioned therein;
triggering the plurality of sensors via the plurality of sensory elements; and
activating the end effector of the at least one handheld surgical instrument directly from motions of the glove as the glove moves directly over one or more surfaces of the at least one handheld surgical instrument.

13. The method according to claim 12, further comprising placing the plurality of sensory elements on a finger region of the glove, a palm region of the glove or a combination thereof.

14. The method according to claim 12, wherein the plurality of sensory elements include at least one of magnetic elements and conductive elements.

15. The method according to claim 12, further comprising incorporating a plurality of textured control surfaces indicating control boundaries on an exterior surface of the at least one handheld surgical instrument.

16. A medical system, comprising:
a wearable article including a plurality of sensory elements incorporated thereon; and
at least one handheld medical device having an end effector and including a plurality of sensors placed therein,
wherein the at least one handheld medical device is devoid of any exterior switches and buttons, and
wherein the at least one handheld medical device is configured to allow wireless communication between the plurality of sensory elements and the plurality of sensors to control the end effector directly from motions of the wearable article as the wearable article moves directly over one or more surfaces of the at least one handheld medical device.

* * * * *